United States Patent
Matsumoto et al.

(10) Patent No.: US 8,026,663 B2
(45) Date of Patent: Sep. 27, 2011

(54) TRIPHENYLENE COMPOUNDS, METHOD OF MANUFACTURING THE SAME AND ORGANIC ELECTROLUMINESCENT DEVICES EMPLOYING THE SAME

(75) Inventors: Hideyuki Matsumoto, Kiryu (JP); Soichiro Kyushin, Kiryu (JP); Keisuke Negishi, Kiryu (JP); Youhei Ono, Ichihara (JP); Manabu Uchida, Ichihara (JP); Hidefumi Oomori, Ichihara (JP)

(73) Assignee: National University Corporation Gunma University, Gunma (JP)

( * ) Notice: Subject to any disclaimer, the term of this patent is extended or adjusted under 35 U.S.C. 154(b) by 1000 days.

(21) Appl. No.: 11/576,593

(22) PCT Filed: Oct. 5, 2005

(86) PCT No.: PCT/JP2005/018727
§ 371 (c)(1), (2), (4) Date: Aug. 24, 2007

(87) PCT Pub. No.: WO2006/038709
PCT Pub. Date: Apr. 13, 2006

(65) Prior Publication Data
US 2008/0265750 A1    Oct. 30, 2008

(30) Foreign Application Priority Data

Oct. 5, 2004   (JP) .................... 2004-292415
Oct. 5, 2004   (JP) .................... 2004-292697

(51) Int. Cl.
*H01L 51/54* (2006.01)
*C09K 11/06* (2006.01)

(52) U.S. Cl. .......... 313/504; 428/690; 428/917; 257/40; 257/E51.049; 313/506

(58) Field of Classification Search .................. None
See application file for complete search history.

(56) References Cited

U.S. PATENT DOCUMENTS 5,294,870 A * 3/1994 Tang et al. ............... 313/504
(Continued)

FOREIGN PATENT DOCUMENTS

JP    11-255781    9/1999
(Continued)

OTHER PUBLICATIONS

Rego et al., Chemical Communications, (1996), pp. 1031-1032.*
(Continued)

*Primary Examiner* — Angela Ortiz
*Assistant Examiner* — Brett A Crouse
(74) *Attorney, Agent, or Firm* — Hogan Lovells US LLP (57) ABSTRACT

The present invention provides a novel compound represented by general formula (I) below, a method of manufacturing the same and an organic electroluminescent device employing the same:

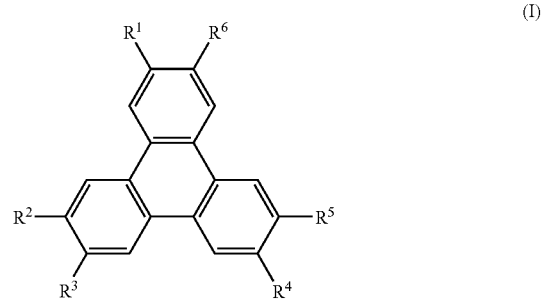

(I)

where $R^1$ to $R^6$ are independent of one another and are each a hydrogen atom or a substituent represented by general formula (II) below, and at least one of $R^1$ to $R^6$ is a substituent represented by general formula (II):

$$-C{\equiv}C-SiR^aR^bR^c \qquad (II)$$

where $R^a$, $R^b$ and $R^c$ are independent of one another and are each an aliphatic hydrocarbon group having 1 to 10 carbon atoms or an aromatic hydrocarbon group.

5 Claims, 7 Drawing Sheets

U.S. PATENT DOCUMENTS

| | | | | |
|---|---|---|---|---|
| 6,097,147 | A | * | 8/2000 | Baldo et al. .................. 313/506 |
| 6,897,913 | B2 | * | 5/2005 | Tsuboyama et al. ............ 349/61 |
| 7,315,341 | B2 | * | 1/2008 | Nimura et al. ................ 349/117 |

FOREIGN PATENT DOCUMENTS

| | | |
|---|---|---|
| JP | 2003-252818 | 9/2003 |
| JP | 2003-252880 | 9/2003 |
| JP | 2004-103463 | 4/2004 |
| WO | WO 99/57222 | 11/1999 |

OTHER PUBLICATIONS

Korishima et al. JP10-321371, (1998), Machine Assisted Translation.*

Baldo et al., "Very high-efficiency green organic light-emitting devices based on electrophosphorescence" Applied Physics Letters, vol. 75, No. 1, pp. 4-6, Jul. 5, 1999.

Holmes et al., "Efficient, deep-blue organic electrophosphorescence by guest charge trapping" Applied Physics Letters, vol. 83, No. 18, pp. 3818-3820, Nov. 3, 2003.

Rego et al., "Synthesis and Characterization of Fluorescent, Low-Symmetry Triphenylene Discotic Liquid Crystals: Tailoring of Mesomorphic and Optical Properties" Chem. Mater. 1996, 8, pp. 1402-1409.

Negishi, et al., "Synthesis, Structure and Properties of Silylethynyltriphenylenes" The Chemical Society of Japan, vol. 85, No. 1, p. 118, 2005.

Negishi, et al., "Synthesis and Properties of Silylethynyl Substituted Triphenylenes" The Society of Silicon Chemistry Japan, No. 21, p. 85, Oct. 2004.

Negishi et at., "Syntheses and Properties of Some Silylethynyl Substituted Triphenylenes" 38th Silicon Symposium, p. 32, Jun. 2005.

Negishi et al., "Synthesis and Properties of Silylethynyl-Substituted Triphenylenes" The 14th International Symposium on Organosilicon Chemistry, p. 214, Jul. 2005.

* cited by examiner

TRIPHENYLENE COMPOUNDS, METHOD OF MANUFACTURING THE SAME AND ORGANIC ELECTROLUMINESCENT DEVICES EMPLOYING THE SAME

TECHNICAL FIELD

The present invention relates to a novel triphenylene compound having a high level of excited triplet energy and containing a silylethynyl group, a method of manufacturing the same and an organic electroluminescent device employing the same.

BACKGROUND ART

There is already known an organic electroluminescent device having a multilayer laminated structure and employing phosphorescence (an organic electroluminescent device employing phosphorescence being hereinafter referred to also as a phosphorescent device) (see U.S. Pat. No. 6,097,147). A device relying solely on fluorescence for emission of light has a theoretical limit of 25% as its internal quantum efficiency, since it employs an excited singlet state, but a phosphorescent device is considered to have a theoretical limit of 100% as its internal quantum efficiency, since excited energy of the triplet state contributes to emission of light. Accordingly, a phosphorescent device is superior to a fluorescent device, as it permits an improvement in luminous efficiency, or the ratio of luminous brightness to driving current density.

A phosphorescent device can be obtained by doping small amount of a phosphorescent dopant in a luminous layer of the host compound of the host compound. The host compound is required to have a higher level of excited triplet state energy than that of the phosphorescent dopant, and the compounds which can be employed are, therefore, limited. For example, the carbazole derivatives as disclosed in Appl. Phys. Lett., 75, 4 (1999), and the compounds as disclosed in JP-A-2004-103463 and Appl. Phys. Lett., 83, 3818 (2003) are used as the phosphorescent host compounds. However, it is considered necessary to develop a novel host compound, since the phosphorescent devices employing the existing phosphorescent host compounds have drawbacks including the necessity for a high driving voltage.

There are known several compounds as triphenylene compounds having substituents containing silicon (see JP-A-2003-252818, JP-A-11-255781 and JP-A-2003-252880). JP-A-2003-252818 and JP-A-255781 disclose compounds having a side chain containing silicon and bonded to a triphenylene backbone by an oxygen atom. JP-A-2003-252880 discloses a compound having a side chain containing silicon and bonded to a triphenylene backbone directly by silicon. However, there has not been known any triphenylene compound having a silylethynyl group. Attempts have been made to isolate a triphenylene compound (terminating at H) having a silylethynyl group by the desilylation reaction of 2,3,6,7,10,11-hexakis(trimethylsilylethynyl)triphenylene, but its isolation has been difficult, as it is unstable in the air and immediately undergoes a polymerization reaction to form a polymeric product.

DISCLOSURE OF THE INVENTION

Under these circumstances, it is an object of the present invention to provide a novel triphenylene compound having a high level of excited triplet energy and containing a silylethynyl group, a method of manufacturing the same and a novel phosphorescent device made by employing the same in its luminous layer and capable of being driven by a low voltage.

As a result of our careful study, we, the inventors of the present invention, have succeeded in manufacturing 2,3,6,7,10,11-hexakis(trimethyl-silylethynyl)triphenylene by reacting 2,3,6,7,10,11-hexabromotriphenylene and trialkylsilylacetylene. We have also found it possible to obtain in a similar way a novel triphenylene compound (hereinafter referred to also as the compound of the present invention) containing that compound and represented by general formula (I) below. We have further found it possible to derive phosphorescence from a luminescent device at a low voltage by employing the compound of the present invention as a host compound in the luminous layer of a phosphorescent device and doping it with a phosphorescent dopant. Our finding of those things has made a basis for the present invention. Thus, the present invention is as claimed below.

(1) A compound represented by general formula (I) below:

(I)

where $R^1$ to $R^6$ are independent of one another and are each a hydrogen atom or a substituent represented by general formula (II) below, and at least one of $R^1$ to $R^6$ is a substituent represented by general formula (II):

$$—C\!\!\equiv\!\!C—SiR^aR^bR^c \quad (II)$$

where $R^a$, $R^b$ and $R^c$ are independent of one another and are each an aliphatic hydrocarbon group having 1 to 10 carbon atoms or an aromatic hydrocarbon group.

(2) A compound as set forth at (1), wherein all of $R^1$ to $R^6$ in general formula (I) are the substituents represented by general formula (II) and $R^a$, $R^b$ and $R^c$ in general formula (II) are independent of one another and are each an aliphatic hydrocarbon group having 1 to 10 carbon atoms.

(3) A compound as set forth at (1), wherein all of the substituents $R^a$, $R^b$ and $R^c$ in general formula (II) are an alkyl group.

(4) A compound as set forth at (3), wherein the alkyl group is an isopropyl or methyl group.

(5) A compound as set forth at (1), wherein any one or two of $R^1$ to $R^6$ in general formula (I) are the substituents represented by general formula (II) and $R^a$, $R^b$ and $R^c$ in general formula (II) are each a phenyl group.

(6) A method of manufacturing a compound represented by general formula (I), characterized in that a compound represented by general formula (III) below is reacted with a compound represented by general formula (IV) below:

(III)

where $R^1$ to $R^6$ are independent of one another and are each a hydrogen, bromine or iodine atom, and at least one of $R^1$ to $R^6$ is a bromine or iodine atom, where $R^a$, $R^b$ and $R^c$ are independent of one another and are each an aliphatic hydrocarbon group having 1 to 10 carbon atoms or an aromatic hydrocarbon group,

(I)

where $R^1$ to $R^6$ are independent of one another and are each H or a substituent represented by general formula (II) below, and at least one of $R^1$ to $R^6$ is a substituent represented by general formula (II):

—C≡C—SiR$^a$R$^b$R$^c$ (II)

where $R^a$, $R^b$ and $R^c$ are independent of one another and are each an aliphatic hydrocarbon group having 1 to 10 carbon atoms or an aromatic hydrocarbon group.

(7) An organic electroluminescent device having at least a pair of electrodes and a luminous layer positioned between the electrodes, and employing phosphorescence, the luminous layer containing at least one compound represented by general formula (I) and a phosphorescent dopant:

(I)

where $R^1$ to $R^6$ are independent of one another and are each a hydrogen atom or a substituent represented by general formula (II) below, and at least one of $R^1$ to $R^6$ is a substituent represented by general formula (II):

—C≡C—SiR$^a$R$^b$R$^c$ (II)

where $R^a$, $R^b$ and $R^c$ are independent of one another and are each an aliphatic hydrocarbon group having 1 to 10 carbon atoms or an aromatic hydrocarbon group.

(8) An organic electroluminescent device employing phosphorescence as set forth at (7), wherein all of $R^1$ to $R^6$ in general formula (I) are the substituents represented by general formula (II) and $R^a$, $R^b$ and $R^c$ in general formula (II) are independent of one another and are each an aliphatic hydrocarbon group having 1 to 10 carbon atoms.

(9) An organic electroluminescent device employing phosphorescence as set forth at (7), wherein all of the substituents $R^a$, $R^b$ and $R^c$ in general formula (II) are an alkyl group.

(10) An organic electroluminescent device employing phosphorescence as set forth at (7), wherein the alkyl group is an isopropyl or methyl group.

(11) An organic electroluminescent device employing phosphorescence as set forth at (7), wherein any one or two of $R^1$ to $R^6$ in general formula (I) are the substituents represented by general formula (II) and $R^a$, $R^b$ and $R^c$ in general formula (II) are each a phenyl group.

(12) An organic electroluminescent device employing phosphorescence as set forth at (7), wherein the phosphorescent dopant is at least one complex selected from iridium, platinum, osmium and gold complexes.

(13) An organic electroluminescent device employing phosphorescence as set forth at (7), further having an electron transport layer, a hole blocking layer, a hole transport layer and a hole injection layer between the pair of electrodes.

The compound of the present invention is stable because of its high heat and light resistance and is high in processability because of its solubility in an organic solvent. The compound of the present invention is useful as an optical material for an organic electroluminescent device or the like owing to its property of emitting fluorescence and phosphorescence.

Moreover, those of the compounds of the present invention which emit phosphorescence are suitable as a host compound in the luminous layer of a phosphorescent device owing to its high excited triplet energy and make it possible to produce a novel phosphorescent device.

BEST MODE OF CARRYING OUT THE INVENTION

The present invention will now be described in detail.

The compound of the present invention is a compound represented by general formula (I).

(I)

where $R^1$ to $R^6$ are independent of one another and are each a hydrogen atom or a substituent represented by general formula (II) below, and at least one of $R^1$ to $R^6$ is a substituent represented by general formula (II). Three to six of $R^1$ to $R^6$ are preferably substituents represented by general formula (II) and all of $R^1$ to $R^6$ are more preferably substituents represented by general formula (II).

The substituents represented by general formula (II) may differ from $R^1$ to $R^6$, but are preferably the same.

(II)

In general formula (II), $R^a$, $R^b$ and $R^c$ are independent of one another and are each an aliphatic hydrocarbon group having 1 to 10 carbon atoms or an aromatic hydrocarbon group, more preferably an aliphatic hydrocarbon group having 1 to 10 carbon atoms and still more preferably an aliphatic hydrocarbon group having 1 to 8 carbon atoms. The aliphatic hydrocarbon group may be saturated or unsaturated, and may be branched. When it is an unsaturated aliphatic hydrocarbon group, it may have a plurality of double bonds. The aliphatic hydrocarbon group is not limited to any specific kind if it has 1 to 10 carbon atoms, but it may be a methyl or ethyl group, or any other substituent as shown below, though an isopropyl or methyl group is, among others, preferred. The aromatic hydrocarbon group may be a phenyl, tolyl or substituted phenyl group, or any other group as shown below. $R^a$, $R^b$ and $R^c$ may be the same or different substituents. When $R^a$, $R^b$ and $R^c$ are all a phenyl group, the number of the substituents represented by general formula (II) in the compound represented by general formula (I) is preferably 1 or 2.

Preferred examples of compounds according to general formula (I) are 2,3,6,7,10,11-hexakis(trimethylsilylethynyl)triphenylene and 2,3,6,7,10,11-hexakis(triisopropylsilylethynyl)triphenylene.

Examples of $R^a$, $R^b$ and $R^c$ are given below, though $R^a$, $R^b$ and $R^c$ are not limited thereto.

(Examples of Alkyl Groups)

—$CH_3$
—$CH_2CH_3$
—$CH_2CH_2CH_3$
—$CH_2CH_2CH_2CH_3$
—$CH_2CH_2CH_2CH_2CH_3$
—$CH_2CH_2CH_2CH_2CH_2CH_3$
—$CH_2CH_2CH_2CH_2CH_2CH_2CH_3$
—$CH_2CH_2CH_2CH_2CH_2CH_2CH_2CH_3$
—$CH_2CH_2CH_2CH_2CH_2CH_2CH_2CH_2CH_3$
—$CH_2CH_2CH_2CH_2CH_2CH_2CH_2CH_2CH_2CH_3$ (The above alkyl groups may be branched as shown by examples below.)

(Examples of Unsaturated Hydrocarbon Groups)

—C≡C—R (R is preferably H, or a straight- or branched-chain alkyl group having 1 to 8 carbon atoms.)

—CH=$CR_2$ (R is preferably H, or a straight- or branched-chain alkyl group having 1 to 8 carbon atoms. When there are different kinds of R, there is no question of cis or trans.)

—$CH_2$—CH=$CR_2$ (R is preferably H, or a straight- or branched-chain alkyl group having 1 to 7 carbon atoms. When there are different kinds of R, there is no question of cis or trans.)

(Phenyl Group)

There is no particular limitation as to the method of manufacturing the compound of the present invention insofar as the compound can be obtained, though the compound can be manufactured by, for example, reacting the compounds according to general formulas (III) and (IV):

(III)

(IV)

In general formula (III), $X^1$ to $X^6$ are independent of one another and are each a hydrogen, bromine or iodine atom, and at least one of $X^1$ to $X^6$ is a bromine or iodine atom. All of $X^1$ to $X^6$ are preferably a bromine atom. The compound (III) can be obtained by, for example, brominating or iodinating triphenylene, as will be shown by examples.

In general formula (IV), $R^a$, $R^b$ and $R^c$ are independent of one another and are each an aliphatic hydrocarbon group having 1 to 10 carbon atoms or an aromatic hydrocarbon group. The aliphatic hydrocarbon group may be saturated or unsaturated, and may be branched. When it is an unsaturated aliphatic hydrocarbon group, it may have a plurality of double bonds. The aliphatic hydrocarbon group is not limited to any specific kind if it has 1 to 10 carbon atoms, but it may be an ethyl, isopropyl or methyl group, or any other substituent as shown above, though an isopropyl or methyl group is, among others, preferred. The aromatic hydrocarbon group may be a phenyl, tolyl or substituted phenyl group, or any other group as shown above. $R^a$, $R^b$ and $R^c$ may be the same or different substituents. The compound (IV) can be obtained by, for example, the Grignard reaction as will be shown by examples.

The reaction of the compounds (III) and (IV) may be carried out in accordance with an ordinary halogen substitution reaction. The reaction is preferably carried out by employing a catalyst. The catalyst is not specifically limited if it can promote the reaction, but it may, for example, be $(PPh_3)_2PdCl_2/CuI$, $(PPh_3)_4Pd/CuI$ or $(PPh_3)_2PdCl_2/CuAc_2$. The solvent to be used for the reaction is not specifically limited if the compounds (III) and (IV) can be dissolved to react with each other, but it may, for example, diisopropylamine, triethylamine, diethylamine or pyridine, or a mixture thereof with benzene or toluene.

The compound obtained by the above reaction can be collected by an ordinary operation for isolation, such as column chromatography. The structure of the compound can be ascertained by X-ray crystal structure analysis, NMR, etc.

The compound of the present invention is applicable as an optical material as for an organic electroluminescent device, since it emits fluorescence and phosphorescence, as will be shown by examples.

Description will now be made of a phosphorescent device made by employing the compound of the present invention.

The phosphorescent device of the present invention is a phosphorescent device having at least a pair of electrodes and a luminous layer positioned between the electrodes, the luminous layer containing at least one compound represented by general formula (I) and a phosphorescent dopant.

For the anode, it is possible to use a metal, alloy, electrically conductive compound, or mixture thereof having a work function exceeding 4 eV. Specific examples thereof are a metal such as Au, CuI, indium tin oxide (hereinafter referred to simply as ITO), $SnO_2$ and ZnO.

For the cathode, it is possible to use a metal, alloy, electrically conductive compound, or mixture thereof having a work function lower than 4 eV. Specific examples thereof are aluminum, calcium, magnesium, lithium, a magnesium alloy and an aluminum alloy. Specific examples of alloys are aluminum/lithium fluoride, aluminum/lithium, magnesium/silver and magnesium/indium. In order to ensure efficient emission by the phosphorescent device, it is desirable for at least one of the electrodes to have a light transmittance of 10% or more. The electrodes preferably have a sheet resistance not exceeding several hundred ohms per square. The electrodes have a thickness of usually from 10 nm to 1 μm and preferably from 10 to 400 nm, depending on their materials. These electrodes can be formed by forming a thin film by e.g. vapor deposition or sputtering from the electrode materials as mentioned above.

The luminous layer of the phosphorescent device according to the present invention contains a compound of general formula (I) as a host compound and further contains a phosphorescent dopant emitting phosphorescence. The compound of general formula (I) which the luminous layer contains may be of one kind, or of two or more kinds. An iridium complex, a platinum complex, an osmium complex and a gold complex can be mentioned as a compound preferred as the phosphorescent dopant, but do not limit it. Specific examples are tris[2-(2-pyridinyl)phenyl-C,N]-iridium (hereinafter expressed by a symbol Ir(ppy)$_3$), bis[(4,6-difluorophenyl)-pyridinate-N,C$^{2'}$]pinacolate iridium, bis(4',6'-difluorophenylpyridinate)-tetrakis(1-pyrazolyl)borate, bis(2-phenylbenzothiazole)iridium acetylacetonate and 2,3,7,8,12,13,17,18-octaethynyl-21H, 2311-porphyrin platinum (II), as stated in Kagaku Kogyo, June 2004, page 13 and references cited therein. The phosphorescent dopant which the luminous layer contains may also be composed of two or more compounds.

The amount of the dopant to be employed differs from one dopant to another and depends on its properties. The standard amount of the dopant may be from 0.001 to 50%, and preferably from 0.1 to 10%, by weight of the total amount of the luminescent materials.

The phosphorescent device of the present invention preferably includes an electron transport layer, a hole blocking layer, a hole transport layer and a hole injection layer, too, between the electrodes.

While the layers of the phosphorescent device according to the present invention are not specifically limited in the order in which they are laid on one another, they are preferably laid in the order of the cathode, electron transport layer, hole blocking layer, hole transport layer, hole injection layer and anode.

Specific examples of the material for the electron transport layer of the phosphorescent device according to the present invention are a quinolinol metal complex, a phenanthroline derivative, a pyridine derivative, an oxadiazole derivative, a triazole derivative, a quinoxaline derivative, a triazine derivative and a borane derivative, but it is not limited thereto. Specific examples of the quinolinol metal complexes are tris (8-hydroxyquinoline)aluminum (hereinafter referred to as Alq3) and bis(2-methyl-8-hydroxyquinoline)-(4-phenylphenol)-aluminum (hereinafter referred to as BAlq). Specific examples of the phenanthroline derivatives are 4,7-diphenyl-1,10-phenanthroline and 2,9-dimethyl-4,7-diphenyl-1,10-phenanthroline (hereinafter referred to as BCP). Specific examples of the pyridine derivatives are 2,5-bis(6'-(2',2''-bipyridyl)-1,1-dimethyl-3,4-diphenylsilyl, 9,10-di(2',2''-bipyridyl)anthracene and 2,5-di(2',2''-bipyridyl)-thiophene.

Specific examples of the material for the hole blocking layer of the phosphorescent device according to the present invention are a quinolinol metal complex, a phenanthroline derivative, an oxadiazole derivative, a triazole derivative, a borane derivative and an anthracene derivative, but it is not limited thereto. Specific examples of the quinolinol metal complexes and phenanthroline derivatives are BAlq and BCP as stated above. A specific example of the oxadiazole derivatives is 2-(4'-tert-butylphenyl)-5-(4''-biphenyl)-1,3,4-oxadiazole. A specific example of the triazole derivatives is 1-phenyl-2-biphenyl-5-para-tert-butylphenyl-1,3,4-triazole. A specific example of the anthracene derivatives is 9,10-bisnaphthylanthracene.

Specific examples of the materials for the hole injection and transport layers of the phosphorescent device according to the present invention are a carbazole derivative, a triarylamine derivative and a phthalocyanine derivative, but they are not limited thereto. Specific examples of the carbazole derivatives are 4,4'-bis(carbazole-9-yl)biphenyl (hereinafter referred to as CBP) and polyvinyl carbazole. Specific examples of the triarylamine derivatives are a polymer having an aromatic tertiary amine in its principal or side chain, 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl (hereinafter referred to as NPD), 4,4',4''-tris{N-(3-methylphenyl)-N-phenylamino}triphenylamine and a starburst amine derivative. Specific examples of the phthalocyanine derivatives are non-metallic phthalocyanine and copper phthalocyanine.

The layers constituting the phosphorescent device of the present invention can be formed by forming a thin film from the material for each layer by e.g. vapor deposition, spin coating or casting. The thickness of the film for each layer is not specifically limited, but depends on the properties of its material, though it may usually be in the range of 2 to 5,000 nm. Vapor deposition is preferably employed for forming a film of the luminescent material, since it facilitates the formation of a film of uniform quality, while hardly allowing any pinhole to be formed therein. When vapor deposition is employed for forming a film, its conditions depend on the luminescent materials employed according to the present invention, the intended crystal and association structures of a cumulative molecular film, etc. The conditions for vapor deposition are preferably selected from a boat heating temperature of 50° C. to 400° C., a vacuum degree of $10^{-6}$ to $10^{-3}$ Pa, a deposition rate of 0.01 to 50 nm/second, a substrate temperature of −150° C. to +300° C. and a film thickness of 5 μm to 5 μm.

The phosphorescent device of the present invention is preferably supported on a substrate irrespective of its structure as described above. The substrate may be of any material having mechanical strength, thermal stability and transparency, and may, for example, be glass or a transparent plastic film.

A method of making a phosphorescent device composed of an anode, a hole injection layer, a hole transport layer, a host compound according to general formula (I) and a dopant (a luminous layer), a hole blocking layer, an electron transport layer and a cathode as described above will now be described for exemplifying a method of making a phosphorescent device by employing a compound of general formula (I) (host compound).

A film of an anode material is formed on an appropriate substrate by vapor deposition to form an anode thereon and films of a hole injection layer and a hole transport layer are formed on the anode. A film of a host compound according to general formula (I) and a dopant is formed thereon by co-deposition to form a luminous layer, a hole blocking layer and an electron transport layer are formed on the luminous layer and a film of a cathode material is formed thereon by vapor deposition to form a cathode, whereby an intended phosphorescent device is obtained. The procedure described above for making a phosphorescent device can be reversed to form its layers in the order of cathode, electron transport layer, hole blocking layer, luminous layer, hole transport layer, hole injection layer and anode.

When a direct-current voltage is applied to the phosphorescent device as obtained above, the anode is employed as the plus pole, and the cathode as the minus pole and the application of a voltage of, say, 2 to 40 V makes it possible to observe emission of light from the transparent or semi-transparent electrode or electrodes (anode or cathode, or both). The phosphorescent device emits light when an alternating-current voltage is applied thereto, too. The alternating current to be applied may be of any waveform.

The present invention will now be described in further detail based on examples.

Example 1

1. Synthesis of 2,3,6,7,10,11-Hexakis(trimethylsilylethynyl)triphenylene—General Formula (V)

The synthesis of 2,3,6,7,10,11-hexakis(trimethylsilylethynyl)triphenylene was performed by the method as described below.

(V)

1.1. Synthesis of Triphenylene

Triphenylene was synthesized by the reaction shown below:

(Materials and Amounts Employed)
2-Bromofluorobenzene (Tokyo Kasei, 99%): 10.12 g/5.73× 10-z mole
Mg (Wako, flaky, 99.5%): 1.54 g/6.30×10$^{-2}$ mole
THF (treated with benzophenoneketyl): 85+15 ml
(Operation and Results)

A 200-ml three-necked flask having a dropping funnel, a Dimroth condenser and a spinner was subjected to flameout treatment and purged with argon. The flask was charged with Mg and it was subjected to two hours of activation at 180° C. The flask was charged with 85 ml of THF, and the dropping funnel with 2-bromofluorobenzene and 15 ml of THF, and their dropping took 20 minutes (the generation of heat started immediately after the dropping was started). The dropping was followed by six hours of refluxing at the THF reflux temperature. After cleansing with a saturated aqueous solution of NH$_4$Cl (100 ml×3), an aqueous phase was extracted with benzene (50 ml×2) and it and an organic phase were combined and dried with anhydrous MgSO$_4$. The removal of the solvent was followed by refining by sublimation and recrystallization, whereby an intended product in the form of colorless transparent needle crystals was obtained in the amount of 789 mg and at a yield of 18%.

1.2. Synthesis of 2,3,6,7,10,11-Hexabromotriphenylene)

2,3,6,7,10,11-Hexabromotriphenylene was synthesized by the reaction shown below:

(Materials and Amounts Employed)
Triphenylene (synthesized): 2.00 g/8.51×10$^{-3}$ mole
Br$_2$ (Wako): 4.0 ml
Fe (powder): 0.484 g/3.29×10$^{-3}$ mole
PhNO$_2$ (Kanto, simple distillate): 80 ml
(Operation and Results)

A 200-ml three-necked flask having a dropping funnel, a Dimroth condenser and a spinner was subjected to flameout treatment and purged with argon. The flask was charged with triphenylene, Fe powder and PhNO$_2$, and the dropping funnel with Br$_2$, and its dropping took 15 minutes. Its dropping was followed by 10 hours of stirring at room temperature and two hours of stirring at 200° C. After its cooling, Et$_2$O was put into the reaction mixture, the insoluble matter was collected by filtration and subjected to recrystallization with 800 ml of o-dichlorobenzene to give an intended white powder in the amount of 5.18 g and at a yield of 87%.

1.3. Synthesis of Trimethylsilylacetylene

Trimethylsilylacetylene was synthesized by the reaction shown below:

(Materials and Amounts Employed)
Acetylene (bottle, Kansan)
EtMgBr (prepared, 1.5 M in THF): 400 ml/600 mmole
Me$_3$SiBr (Chisso, 99%): 85.54 g/553 mmole
THF (treated with benzophenoneketyl): 200 ml
(Operation and Results)

A 2000-ml four-necked flask having a dropping funnel, a Dimroth condenser and a spinner was subjected to flameout treatment and purged with argon. The flask was charged with 200 ml of THF. After 1.5 hours of acetylene gas bubbling in an ice bath, EtMgBr, which had been prepared beforehand, was dropped from the dropping funnel and its dropping took one hour and 50 minutes. Its dropping was followed by 30 minutes of stirring with bubbling and 40 minutes of stirring without bubbling. The bath was changed to a dry ice-methanol bath and the dropping of Me$_3$SiBr from the dropping funnel took 40 minutes. After 30 minutes of stirring in the dry ice-methanol bath, room temperature was restored and stirring was continued overnight. The bath was changed to an ice bath again and 200 ml of a saturated aqueous solution of ammonium chloride was put thereinto to terminate the reaction. An organic phase was collected by separating the liquid and was dried with anhydrous MgSO$_4$. By distillation at normal pressure and fractionation by a fractionating column, there was obtained trimethylsilylacetylene as an intended compound in the form of a colorless transparent liquid.

1.4. Preparation of Dichlorobis(triphenylphosphine)palladium (II)

Dichlorobis(triphenylphosphine)palladium (II) was synthesized by the reaction shown below:

(Materials and Amounts Employed)
PdCl$_2$ (Wako, 98%): 1.00 g/5.54×10$^{-3}$ mole
PPh$_3$ (Kanto, 99%): 3.00 g/1.14×10$^{-2}$ mole
Conc. HCl aq. (Kanto, 35-37%): 0.17 ml
EtOH (simple distillate): 50 ml
H$_2$O (ion-exchanged water): 100 ml
(Operation and Results)

A 200-ml three-necked flask was charged with ion-exchanged water, concentrated hydrochloric acid and PdCl$_2$ and they were slowly dropped into an EtOH solution of PPh$_3$ under stirring by employing a cannula (while it was heated to 60° C. in an oil bath). Their dropping was followed by three hours of stirring at 60° C. Insoluble matter (intended product) was collected by filtration and was cleansed with 100 ml of boiled water, then 100 ml of hot EtOH and then 100 ml of hot Et$_2$O (a gross amount of 2.09 g was obtained at a gross yield of 53%). One gram thereof was dissolved in 50 ml of hot CHCl$_3$ and 150 ml of hexane was put thereinto, whereby (PPh$_3$)$_2$PdCl$_2$ was precipitated. The (PPh$_3$)$_2$PdCl$_2$ was dried under heat at 100° C. by using phosphorus pentachloride (0.83 g of yellow finely divided crystals were recovered at a rate of 83%).

1.5. Synthesis of 2,3,6,7,10,11-Hexakis(trimethylsilylethynyl)triphenylene 2, 3, 6, 7, 10, 11-Hexakis(trimethylsilylethynyl)triphenylene was synthesized by the reaction shown below:

1

(Materials and Amounts Employed)
2,3,6,7,10,11-Hexabromotriphenylene: 205 mg/2.92×10$^{-4}$ mole
Trimethylsilylacetylene: 1.68 g 11.71×10$^{-2}$ mole
(PPh$_3$)$_2$PdCl$_2$: 245 mg/3.49×10$^{-4}$ mole
CuI (Wako): 66 mg/3.47×10$^{-4}$ mole
i-Pr$_2$NH (Tokyo Kasei, distilled from CaH$_2$): 200 ml (Operation and Results)

A 300-ml three-necked flask having a dropping funnel, a Dimroth condenser and a spinner was subjected to flameout treatment and purged with N$_2$. The flask was charged with 2,3,6,7,10,11-hexabromotriphenylene, (PPh$_3$)$_2$PdCl$_2$, CuI and i-Pr$_2$NH. The dropping funnel dropped Me$_3$SiC≡CH in 30 minutes (the solution turned from yellow to brown immediately). Then, stirring was continued for three hours under reflux. After the solvent was removed by a rotary evaporator, insoluble matter was removed by a flush column (Wako Gel C-60, benzene) and fractionation was carried out by a wet column (firstly, Wako Gel C-60, hexane/Et$_2$O=9/1; secondly, Wako Gel C-60, hexane/CH$_2$Cl$_2$=8/2), whereby 2,3,6,7,10, 11-hexakis(trimethylsilylethynyl)triphenylene was obtained as a yellow crystal in the amount of 210 mg at a yield of 90%.

2. Analysis of 2,3,6,7,10,11-Hexakis(trimethylsilylethynyl)triphenylene 2.1. X-Ray Crystal Structure Analysis Identification was made with various spectra and a decision on structure was finally made by X-ray crystal structure analysis.

The spectral data of 2,3,6,7,10,11-hexakis(trimethylsilylethynyl)-triphenylene were as follows:

MS (Mass spectrometry) (EI, 70 eV) m/z (%) 804 (M$^+$, 83), 789 (3), 731 (3), 716 (7), 701 (8), 73 (100)

IR (Infrared absorption spectrum) (KBr)cm$^{-1}$ 2959, 2899, 2162, 1483, 1404, 1248, 1190, 1146, 997, 864, 845, 760, 650

$^1$H NMR (Nuclear magnetic resonance spectrum) (500 MHz, CDCl$_3$) δ 0.34 (s, 54H), 8.63 (s, 6H) ppm $^{13}$C NMR (126 MHz, CDCl$_3$) δ 0.06, 99.88, 103.03, 124.91, 127.91, 128.51 ppm $^{29}$Si NMR (99 MHz, CDCl$_3$) δ-17.2 ppm Melting point 300° C. (decomposition and polymerization)

Figure 1:
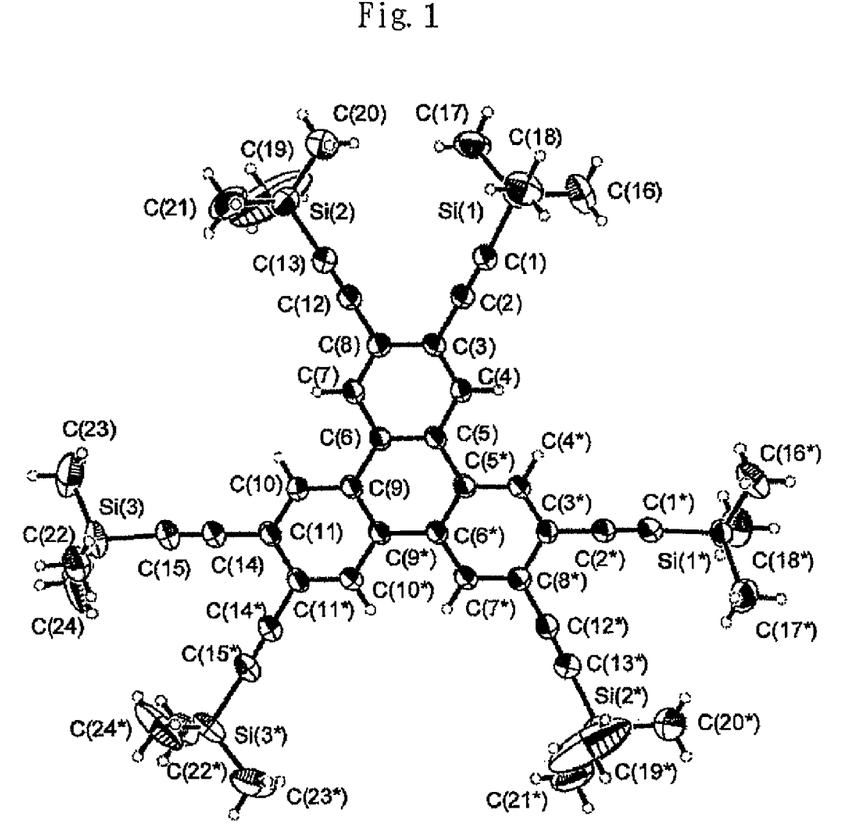
FIG. 1 is an ORTEP diagram (as viewed from top) showing the result of X-ray crystal structure analysis of 2,3,6,7,10,11-hexakis(trimethylsilylethynyl)-triphenylene.
Figure 2:
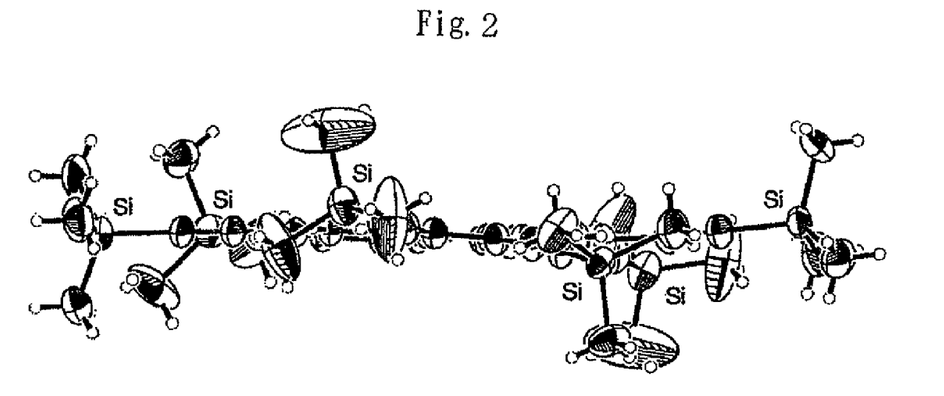
FIG. 2 is an ORTEP diagram (as viewed from side) showing the result of X-ray crystal structure analysis of 2,3,6,7,10,11-hexakis(trimethylsilylethynyl)-triphenylene.
Figure 3:
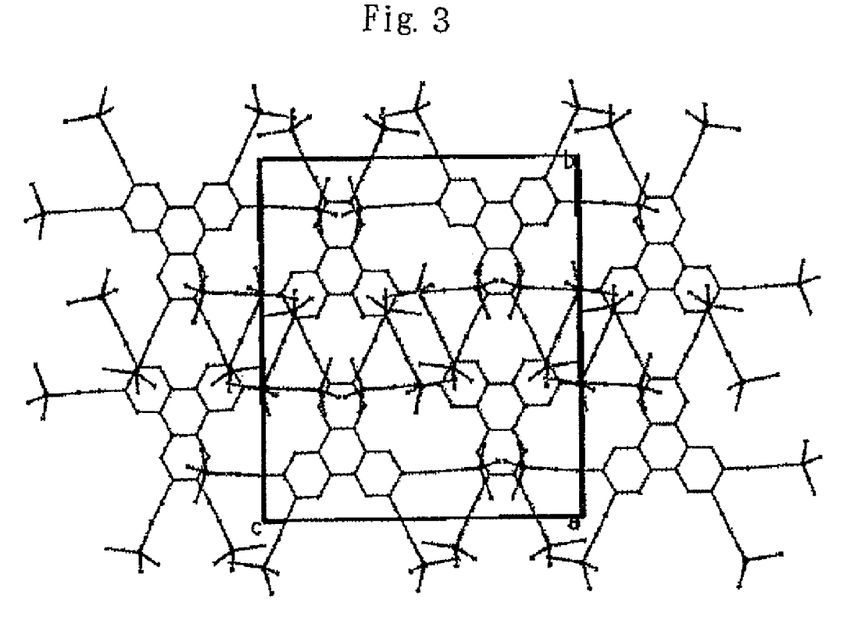
FIG. 3 is an ORTEP diagram (as viewed along the a-axis) showing the result of X-ray crystal structure analysis of 2,3,6,7,10,11-hexakis(trimethyl-silylethynyl)triphenylene.
Figure 4:
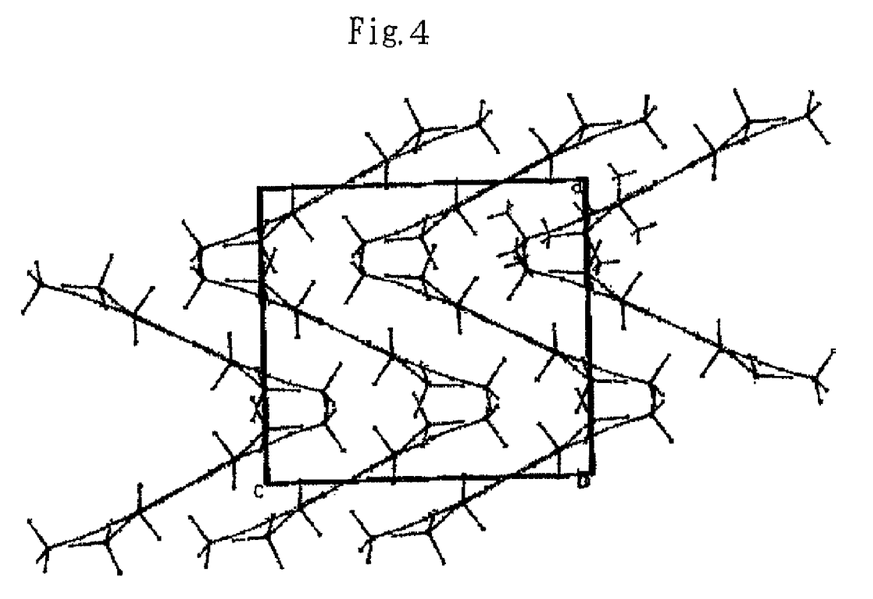
FIG. 4 is an ORTEP diagram (as viewed along the b-axis) showing the result of X-ray crystal structure analysis of 2,3,6,7,10,11-hexakis(trimethyl-silylethynyl)triphenylene.
Figure 5:
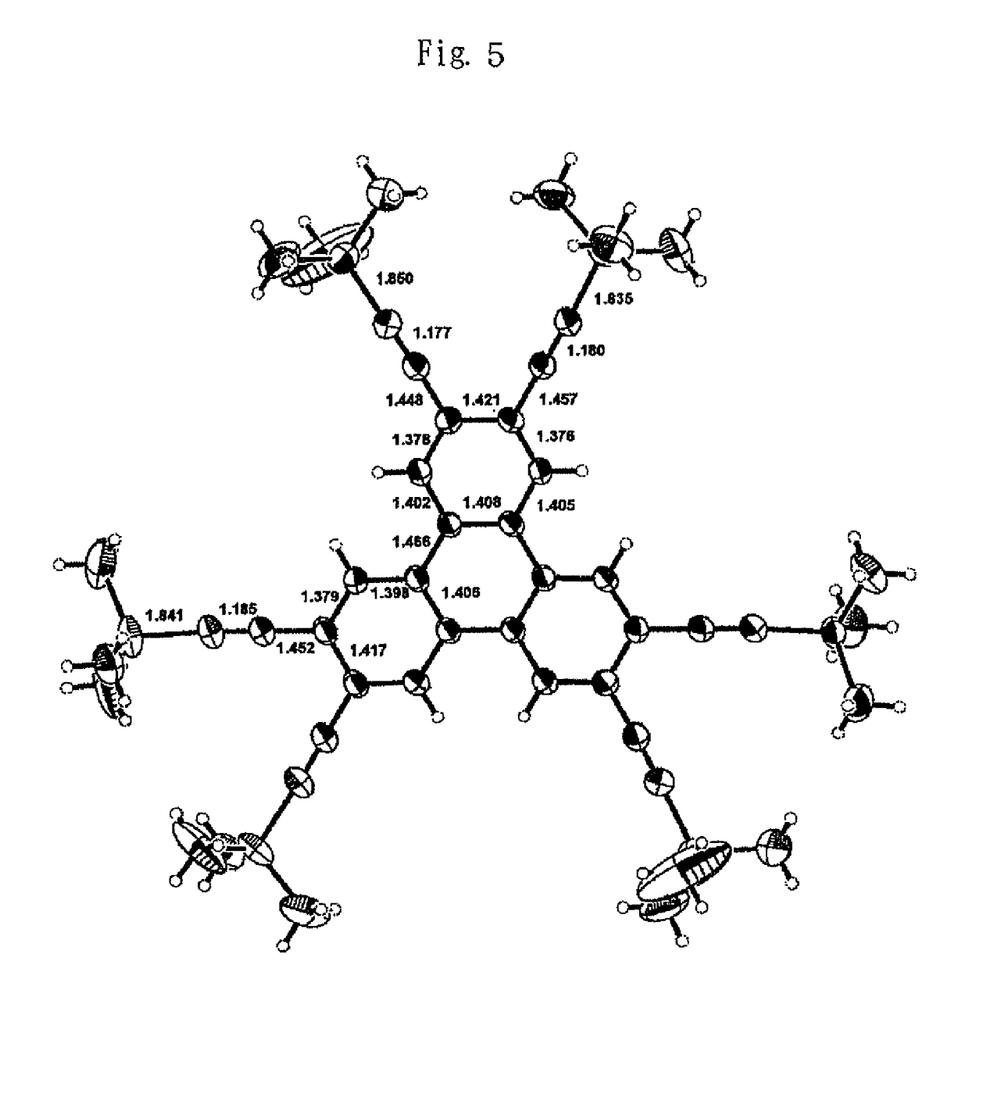
FIG. 5 is a diagram showing the bond distances of 2,3,6,7,10,11-hexakis-(trimethylsilylethynyl)triphenylene.
Figure 6:
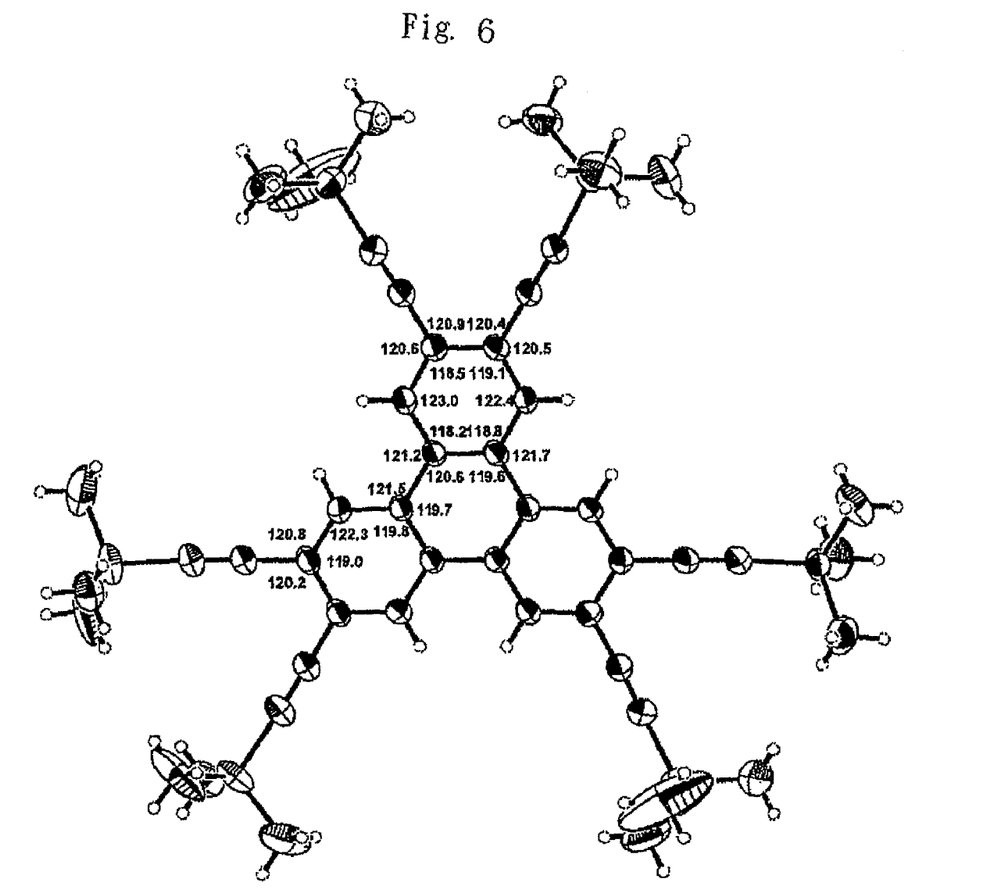
FIG. 6 is a diagram showing the bond angles of 2,3,6,7,10,11-hexakis-(trimethylsilylethynyl)triphenylene.

Yellow transparent crystals of 2,3,6,7,10,11-hexakis-(trimethylsilylethynyl)triphenylene were obtained by recrystallization from a solvent mixture of dichloromethane, hexane and ethanol. FIGS. 1 to 4 show the results of its X-ray crystal structure analysis. The triphenylene ring had a substantially planar structure, but the trimethylsilylethynyl group was found somewhat deviating from the plane of the ring. The bond distances and angles are summarized in FIGS. 5 and 6. The aromatic ring had a longer bond distance between the substituents bonded to each other. The carbon-carbon triple bond had a distance (av. 1.181 Å) slightly shorter than an ordinary value (1.2 Å). A disorder of carbon was found in the trimethylsilyl group at one location. The packing of the molecules showed them lying in a herring-bone pattern. The closest distance between the molecule layers situated in parallel to each other was 4.5 Å between sp carbon. The diagonally situated silicon atoms had a distance of about 16 Å.

2.2. Properties of 2,3,6,7,10,11-Hexakis(trimethylsilyl ethynyl)triphenylene 2.2.1. Physical Properties 2,3,6,7,10,11-Hexakis(trimethylsilylethynyl)triphenylene did not show any definite melting point, but when it was heated to about 300° C., its crystal color turned orange, and when it was further heated, its color turned brown at about 400° C. (as observed by a melting-point measuring instrument). This indicated the possibility of polymerization occurring in the crystals and subsequently thermal weight analysis confirmed the occurrence of polymerization.

As regards solubility, it is considered an improvement over original triphenylene. It is soluble in an ordinary organic solvent (hexane, benzene, toluene, acetone, $Et_2O$, THF, $CH_2Cl_2$ or $CHCl_3$) and sparingly soluble in EtOH or MeOH.

It does not change in transparency, etc. even if its crystals may be left to stand in the air.

2.2.2. Ultraviolet-Visible Absorption Spectra

Figure 7:
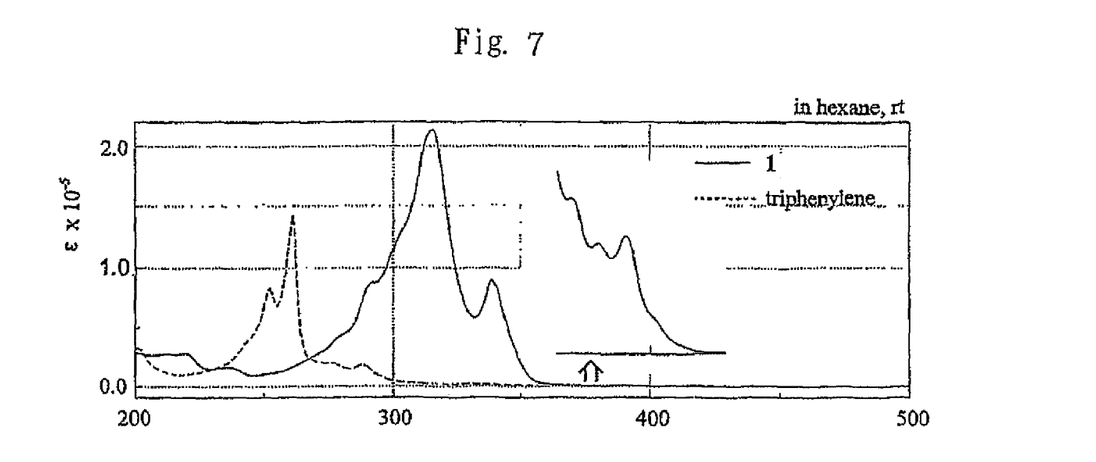
FIG. 7 is a diagram showing the ultraviolet-visible absorption spectra of 2,3,6,7,10,11-hexakis(trimethylsilylethynyl) triphenylene and triphenylene.

FIG. 7 shows the ultraviolet-visible absorption spectra of 2,3,6,7,10,11-hexakis(trimethylsilylethynyl)triphenylene and triphenylene as determined in hexane at room temperature. The absorption maximum and molar absorption coefficient ($\epsilon$) of each absorption band are summarized in Table 1. As is obvious therefrom, the peaks of 2,3,6,7,10,11-hexakis-(trimethylsilylethynyl)triphenylene are all shifted by about 40 to 50 nm to a longer wavelength. Its molar absorption coefficient has greater values, too.

TABLE 1

Ultraviolet-visible absorption spectra of 2,3,6,7,10,11-hexakis(trimethylsilylethynyl)triphenylene and triphenylene

| Compound | $^1B_b$ absorption band $\lambda_{max}(\epsilon)$/nm | $^1L_a$ absorption band $\lambda_{max}(\epsilon)$/nm | $^1L_b$ absorption band $\lambda_{max}(\epsilon)$/nm |
|---|---|---|---|
| 2,3,6,7,10,11-hexakis(tri-methylsilyl-ethynyl)tri-phenylene | 315 (214000) 292 (87500) | 339 (89300) | 403 (sh) (240) 390 (850) 380 (800) 370 (1120) |
| Triphenylene | 257 (147700) 249 (85700) 241 (sh) (40500) | 285 (18100) 273 (20200) | 346 (sh) (40) 335 (290) 327 (250) 320 (370) |

2.2.3. Luminescence (Fluorescence and Phosphorescence) Spectra

Figure 8:
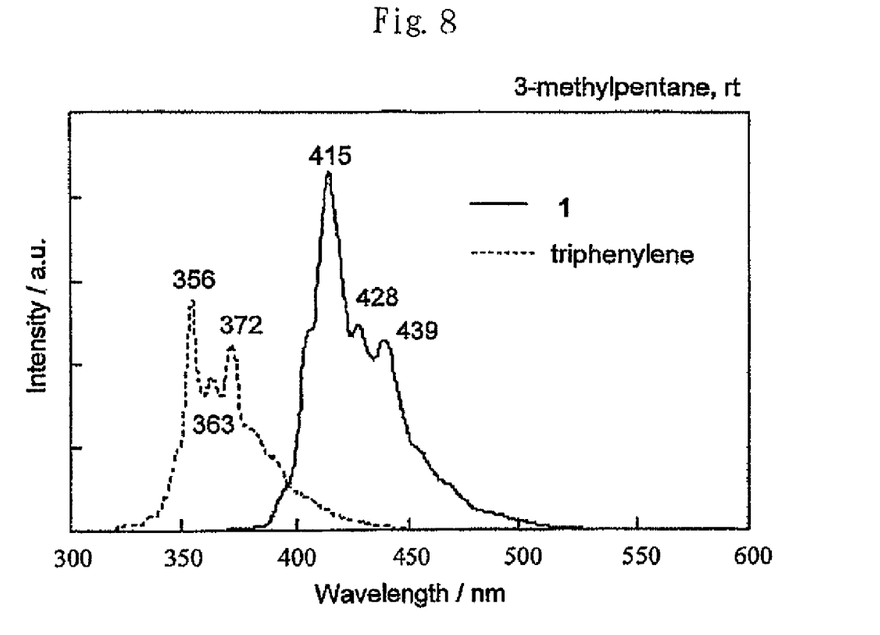
FIG. 8 is a diagram showing the fluorescence spectra of 2,3,6,7,10,11-hexakis(trimethylsilylethynyl)triphenylene and triphenylene.

FIG. 8 shows the fluorescence spectra of 2,3,6,7,10,11-hexakis(trimethylsilylethynyl)triphenylene and triphenylene as determined in 3-methylpentane (3-MP) after deaeration and sealing at room temperature with an excitation wavelength of 296 nm. The fluorescence maximum is at 415, 428 and 439 nm, all shifted by about 60 nm to a longer wavelength from the corresponding fluorescence maximum of triphenylene, and is higher in intensity, too. The quantum yield of fluorescence is $\Phi_f=0.16$ based on that of triphenylene ($\Phi_f=0.09$).

Figure 9:
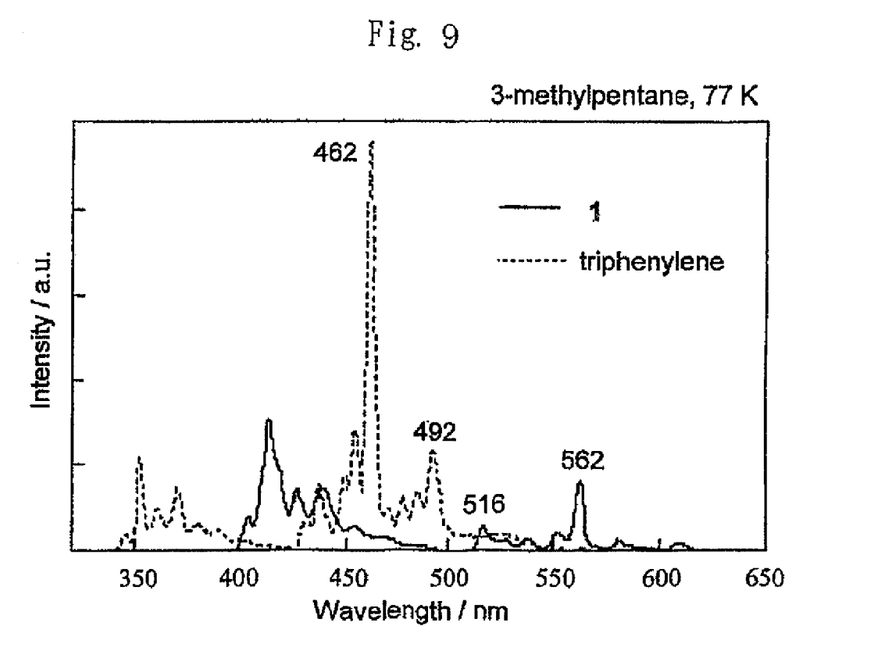
FIG. 9 is a diagram showing the luminescence spectra of 2,3,6,7,10,11-hexakis(trimethylsilylethynyl)triphenylene and triphenylene as determined in 3-MP after degassed and sealing at an excitation wavelength of 296 nm and 77 K.

FIG. 9 shows the luminescence spectra of 2,3,6,7,10,11-hexakis-(trimethylsilylethynyl)triphenylene and triphenylene as determined in 3-MP after deaeration and sealing at an excitation wavelength of 296 nm and 77 K. The luminescence maximum was observed at wavelengths all shifted by about 60 nm to longer wavelengths. This confirmed that 2,3,6,7,10,11-hexakis-(trimethylsilylethynyl)triphenylene could be used for the luminous layer of a phosphorescent device.

Example 2

Synthesis and Spectral Analysis of 2,3,6,7,10,11-Hexakis(triisopropylsilylethynyl)triphenylene Triisopropylsilylacetylene was first synthesized by the reaction shown below:

This was reacted with 2,3,6,7,10,11-hexabromotriphenylene to synthesize 2,3,6,7,10,11-hexakis(triisopropylsilylethynyl)triphenylene (general formula (VI)). The reaction was similar to that employed for 2,3,6,7,10,11-hexakis-(trimethylsilylethynyl)triphenylene. The yield was 55%.

(VI)

Figure 10:
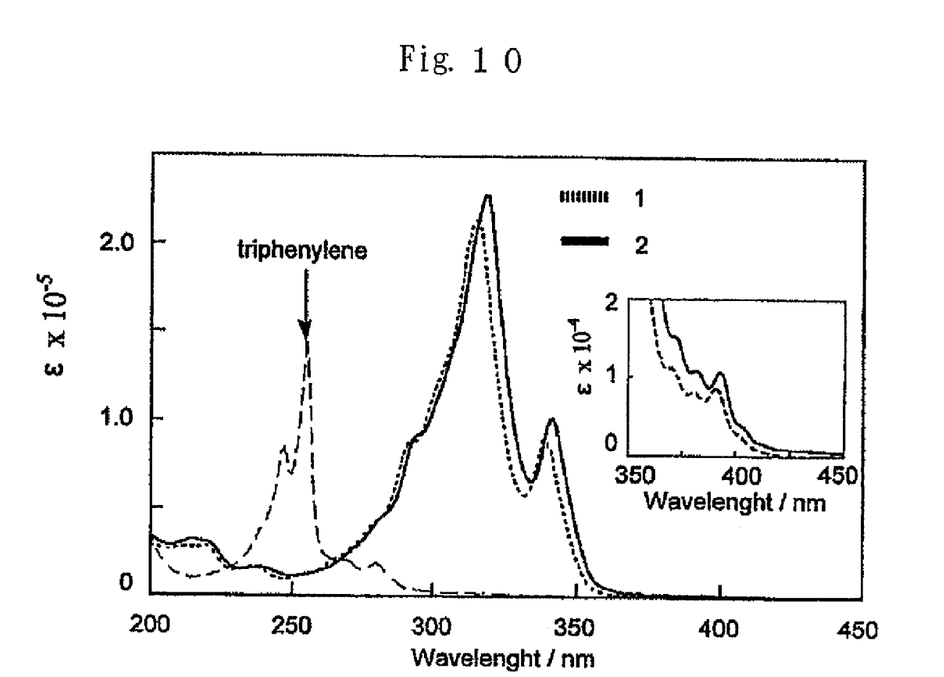
FIG. 10 is a diagram showing the ultraviolet-visible absorption spectra of triphenylene compounds, in which 1 indicates 2,3,6,7,10,11-hexakis-(trimethylsilylethynyl)triphenylene and 2 indicates 2,3,6,7,10,11-hexakis-(triisopropylsilylethynyl)triphenylene.

The ultraviolet-visible absorption spectra of 2,3,6,7,10,11-hexakis-(triisopropylsilylethynyl)triphenylene were determined in hexane at room temperature. The results are shown in FIG. 10 with data on triphenylene and 2,3,6,7,10,11-hexakis(trimethylsilylethynyl)triphenylene.

A shift to a longer wavelength was observed with 2,3,6,7,10,11-hexakis(triisopropylsilylethynyl)triphenylene, too, as compared with triphenylene.

Figure 11:
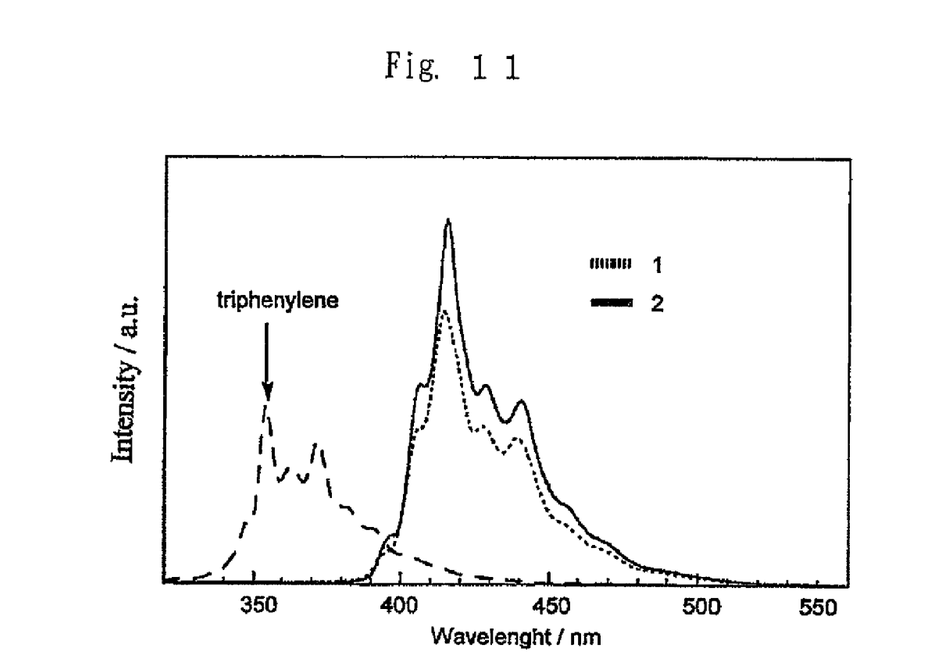
FIG. 11 is a diagram showing the fluorescence spectra of triphenylene compounds, in which 1 indicates 2,3,6,7,10,11-hexakis(trimethyl-silylethynyl)triphenylene and 2 indicates 2,3,6,7,10,11-hexakis(triisopropylsilylethynyl)triphenylene.

The fluorescence spectra of 2,3,6,7,10,11-hexakis (triisopropyl-silylethynyl)triphenylene were determined in 3-methylpentane (3-MP) after degassed and sealing at room temperature with an excitation wavelength of 296 nm. The results are shown in FIG. 11 with data on triphenylene and 2,3,6,7, 10,11-hexakis(trimethylsilylethynyl)triphenylene.

Figure 12:
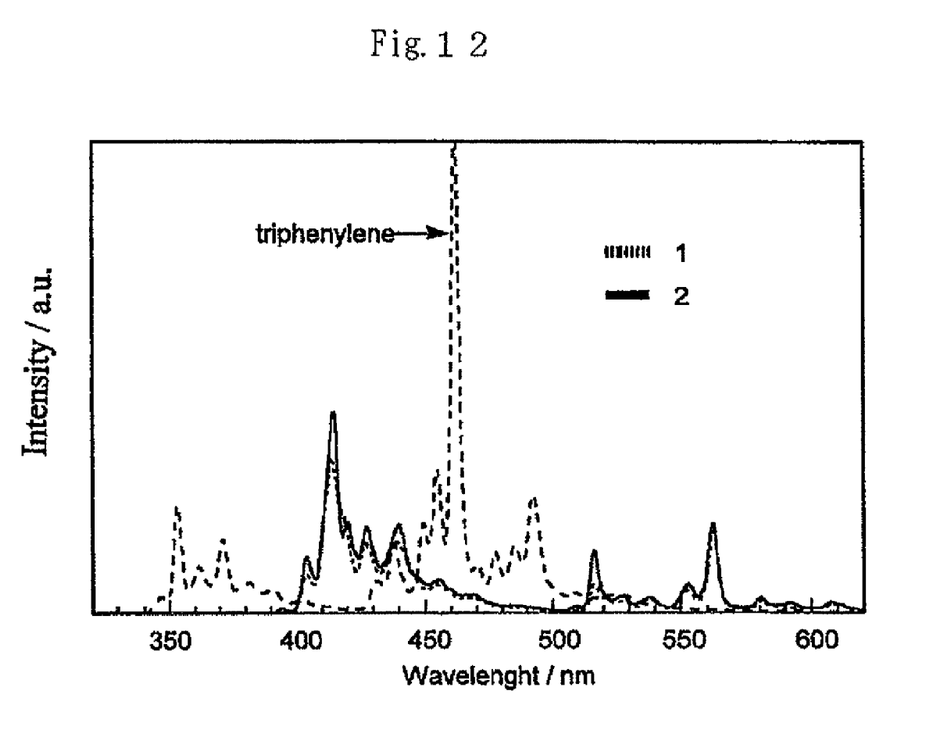
FIG. 12 is a diagram showing the luminescence spectra of triphenylene compounds as determined in 3-MP after deaeration and sealing at an excitation wavelength of 296 nm and 77 K, in which 1 indicates 2,3,6,7,10,11-hexakis-(trimethylsilylethynyl)triphenylene and 2 indicates 2,3,6,7,10,11-hexakis-(triisopropylsilylethynyl)triphenylene.

A shift of about 60 nm to a wavelength longer than the fluorescence maximum of triphenylene and higher intensity were ascertained with 2,3,6,7,10,11-hexakis(triisopropylsilyl-ethynyl)triphenylene, too, The luminescence (fluorescence and phosphorescence) spectra of 2, 3, 6, 7, 10, 11-hexakis(triisopropylsilyl-ethynyl) triphenylene were determined in 3-MP after degassed and sealing at an excitation wavelength of 296 nm and 77 K. The results are shown in FIG. 12 with data on triphenylene and 2,3,6,7,10,11-hexakis(trimethylsilylethynyl)triphenylene A shift to a longer wavelength was observed with 2,3,6,7, 10,11-hexakis-(triisopropylsilylethynyl)triphenylene, too. This confirmed that 2,3,6,7,10,11-hexakis(triisopropylsilyl-ethynyl)triphenylene could be used for the luminous layer of a phosphorescent device.

Example 3

Manufacture of a Phosphorescent Device Including 2,3,6,7,10,11-hexakis-(trimethylsilylethynyl)triphenylene (Compound 1) as a Host Compound and Confirmation of Emission A transparent supporting substrate was prepared by forming a layer of ITO having a thickness of 150 nm on a glass substrate by vapor deposition. The transparent supporting substrate was fixed to a substrate holder in an evaporator, and the evaporator was furnished with an evaporation boat of molybdenum containing copper phthalocyanine (hereinafter expressed by symbol CuPc), an evaporation boat of molybdenum containing NPD, an evaporation boat of molybdenum containing Ir(ppy)3, an evaporation boat of molybdenum containing Compound 1, an evaporation boat of molybdenum containing BCP, an evaporation boat of molybdenum containing Alq3, an evaporation boat of molybdenum containing lithium fluoride and an evaporation boat of tungsten containing aluminum.

A vacuum tank had its pressure reduced to $1 \times 10^{-3}$ Pa, the evaporation boat containing CuPc was heated to deposit a film having a thickness of 25 nm to form a hole injection layer and the evaporation boat containing NPD was heated to deposit a film having a thickness of 35 nm to form a hole transport layer. Then, the boat containing Ir(ppy)3 and the boat containing Compound 1 were heated together to deposit a film having a thickness of 35 nm to form a luminous layer. Then, the boat containing BCP was heated to deposit a film having a thickness of 10 nm to form a hole blocking layer. The evaporation rate was so controlled as to achieve an Ir(ppy)$_3$ to Compound 1 weight ratio of 5 to 95. Then, the evaporation boat containing Alq3 was heated to deposit a film having a thickness of 40 nm to form an electron transport layer.

An evaporation rate of 0.001 to 3.0 nm/sec. was employed for each layer. Then, the evaporation boat containing lithium fluoride was heated to deposit a film having a thickness of 0.5 nm at an evaporation rate of 0.003 to 0.01 nm/sec. and the evaporation boat containing aluminum was heated to deposit a film having a thickness of 100 nm at an evaporation rate of 0.1 to 1 nm/sec., whereby a phosphorescent device was obtained.

The application of a direct-current voltage of 7 V to the ITO electrode as the anode and the lithium fluoride/aluminum electrode as the cathode resulted in an electric current of about 3.0 mA/cm$^2$ and enabled the emission of green light having a spectrum having a peak at a wavelength of 510 nm and representing Ir(ppy)3.

Comparative Example 1

A phosphorescent device was produced by substituting CBP for Compound 1 for the luminous layer in Example 1 and otherwise repeating Example 1.

The application of a direct-current voltage of 7 V to the ITO electrode as the anode and the lithium fluoride/aluminum electrode as the cathode resulted in an electric current of about 1.5 mA/cm$^2$ and enabled the emission of green light having a spectrum having a peak at a wavelength of 510 nm and representing Ir(ppy)3.

The invention claimed is:

1. An organic electroluminescent device having at least a pair of electrodes and a luminous layer positioned between the electrodes, and employing phosphorescence, the luminous layer containing at least one compound represented by general formula (I) and a phosphorescent dopant:

(I)

where $R^1$ to $R^6$ are independent of one another and are each a substituent represented by general formula (II) below:

—C≡C—SiR$^a$R$^b$R$^c$ (II)

where $R^a$, $R^b$ and $R^c$ are independent of one another and are each an aliphatic hydrocarbon group having 1 to 10 carbon atoms.

2. An organic electroluminescent device employing phosphorescence as claimed in claim 1, wherein all of the substituents $R^a$, $R^b$ and $R^c$ in general formula (II) are an alkyl group.

3. An organic electroluminescent device employing phosphorescence as claimed in claim 2, wherein the alkyl group is an isopropyl or methyl group.

4. An organic electroluminescent device employing phosphorescence as claimed in claim 1, wherein the phosphorescent dopant is at least one complex selected from iridium, platinum, osmium and gold complexes.

5. An organic electroluminescent device employing phosphorescence as claimed in claim 1, further having an electron transport layer, a hole blocking layer, a hole transport layer and a hole injection layer between the pair of electrodes.

* * * * *